US008981171B2

(12) United States Patent
Hagemeister et al.

(10) Patent No.: US 8,981,171 B2
(45) Date of Patent: Mar. 17, 2015

(54) PROCESS FOR THE PURIFICATION OF PARAXYLENE

(71) Applicant: ExxonMobil Chemical Patents Inc., Baytown, TX (US)

(72) Inventors: Mark P. Hagemeister, Houston, TX (US); David L. Johnson, Doylestown, PA (US); John J. Monson, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/864,946

(22) Filed: Apr. 17, 2013

(65) Prior Publication Data
US 2013/0237737 A1 Sep. 12, 2013

Related U.S. Application Data

(60) Division of application No. 13/559,215, filed on Jul. 26, 2012, now Pat. No. 8,507,744, which is a continuation of application No. 12/755,571, filed on Apr. 7, 2010, now Pat. No. 8,252,967.

(60) Provisional application No. 61/169,070, filed on Apr. 14, 2009.

(51) Int. Cl.
*C07C 2/22* (2006.01)
*C07C 1/24* (2006.01)
*C07C 2/86* (2006.01)
*C07C 7/14* (2006.01)

(52) U.S. Cl.
CPC . *C07C 2/864* (2013.01); *C07C 7/14* (2013.01); *C07C 2529/40* (2013.01); *C07C 2529/70* (2013.01)
USPC .............................. 585/467; 585/454; 585/469

(58) Field of Classification Search
CPC .......... C07C 2/864; C07C 15/08; C07C 7/12; C07C 2529/40
USPC .......................................... 585/467, 454, 469
See application file for complete search history.

(56) References Cited

U.S. PATENT DOCUMENTS

| 3,462,508 | A | 8/1969 | Dresser et al. |
| 3,558,730 | A | 1/1971 | Neuzil |
| 3,643,453 | A | 2/1972 | Groothuis et al. |
| 3,662,013 | A | 5/1972 | Machell et al. |
| 3,686,343 | A | 8/1972 | Bearden, Jr. et al. |
| 4,002,698 | A | 1/1977 | Kaeding |
| 4,067,920 | A | 1/1978 | Kaeding |
| 4,120,911 | A | 10/1978 | Davidson |
| 4,356,338 | A | 10/1982 | Young |
| 4,423,266 | A | 12/1983 | Young |
| 5,675,047 | A | 10/1997 | Beck et al. |
| 5,804,690 | A | 9/1998 | Chang et al. |
| 5,811,629 | A | 9/1998 | Hubbell et al. |
| 5,939,597 | A | 8/1999 | Dessau et al. |
| 6,028,238 | A | 2/2000 | Beck et al. |
| 6,046,372 | A | 4/2000 | Brown et al. |
| 6,048,816 | A | 4/2000 | Brown et al. |
| 6,156,949 | A | 12/2000 | Brown et al. |
| 6,399,846 | B1 | 6/2002 | MacPherson et al. |
| 6,423,879 | B1 | 7/2002 | Brown et al. |
| 6,504,072 | B1 | 1/2003 | Brown et al. |
| 6,506,954 | B1 | 1/2003 | Brown et al. |
| 6,538,167 | B1 | 3/2003 | Brown et al. |
| 6,642,426 | B1 | 11/2003 | Johnson et al. |
| 7,321,072 | B2 | 1/2008 | Breen et al. |
| 7,439,412 | B2 | 10/2008 | Ou et al. |
| 7,989,672 | B2 | 8/2011 | Kinn et al. |
| 8,283,510 | B2 | 10/2012 | Kinn et al. |
| 8,502,008 | B2 | 8/2013 | Kinn et al. |

FOREIGN PATENT DOCUMENTS

| WO | WO 98/14415 | 4/1998 |
| WO | WO 00/69796 | 11/2000 |

OTHER PUBLICATIONS

I. Kiricsi et al., "*Alkylation of Toluene with Methanol over a Zeolite Disc Synthesized Through Solid State Reactions*", Reaction Kinetics and Catalysis Letter, 1997, vol. 60, No. 1, pp. 89-92.

D. Vu et al., "*Selective Formation of Para-xylene Over H-ZSM-5 Coated with Polycrystalline Silicalite Crystals*", Journal of Catalysis, 2006, vol. 243, pp. 389-394.

*Primary Examiner* — Thuan D Dang

(57) ABSTRACT

The proposed process uses crystallization technology to purify paraxylene simultaneously of large concentrations of C8 aromatics and also small concentrations of oxygenated species.

10 Claims, No Drawings

PROCESS FOR THE PURIFICATION OF PARAXYLENE

CROSS REFERENCE TO RELATED APPLICATIONS

This application is a divisional of U.S. Application No. 13/559,215, filed Jul. 26, 2012, which is a continuation of U.S. Pat. No. 8,252,967, filed Apr. 7, 2010, which claims priority to U.S. Provisional Application Serial No. 61/169,070, filed Apr. 14, 2009, the disclosures of which are fully incorporated herein by reference.

FIELD OF THE INVENTION

The invention relates to a process for the purification of paraxylene by crystallization.

BACKGROUND OF THE INVENTION

Of the xylene isomers, para-xylene (often abbreviated PX) is of particular value since it is useful in the manufacture of terephthalic acid which is an intermediate in the manufacture of synthetic fibers. Equilibrium mixtures of xylene isomers either alone or in further admixture with ethylbenzene generally contain only about 24 wt % para-xylene and separation of p-xylene from such mixtures has typically required superfractionation and multistage refrigeration steps. Such processes have involved high operation costs and resulted in only limited yields.

Crystallization technology has been used to purify paraxylene commercially. The paraxylene streams currently purified using crystallization are not made via alkylation of toluene with methanol and thus do not contain significant concentrations of oxygenates.

During the past decade or more an improved process of toluene alkylation has been developed using as catalysts certain porous crystalline materials, preferably having specific and closely defined diffusion characteristics, such as can be obtained by unusually severe steaming of ZSM-5 containing an oxide modifier. Under appropriate conditions, these catalysts exhibit improved selectivity for the alkylation of toluene with methanol such that the xylene product contains at least about 90% of the paraisomer isomer at per-pass toluene conversions of at least about 15%. This important development has been described in numerous patents and publications, such as U.S. Pat. Nos. 4,002,698; 4,356,338; 4,423,266; 5,675,047; 5,804,690; 5,939,597; 6,028,238; 6,046,372; 6,048,816; 6,156,949; 6,423,879; 6,504,072; 6,506,954; 6,538,167; and 6,642,426.

The paraxylene-rich stream produced by alkylation of toluene with methanol using the aforementioned steamed porous crystalline material has both high concentrations of C8 aromatics (o-xylene, m-xylene, styrene, ethylbenzene, etc.) and low but significant concentrations of oxygenated species (acetic acid, phenol, cresols, etc). Previous processes of making paraxylenes by alkylation did not have significant quantities of oxygenates, accordingly this problem and its magnitude was unexpected.

There are a number of possibilities that come to mind in purifying these feedstreams once the impurities have been identified.

For instance, one could use a combination of processes to first remove low concentrations of oxygenates (e.g. extraction, absorption, etc.) and then a second process to remove high concentrations of C8 aromatics (e.g. simulated countercurrent absorption). However, this is energy and time-inefficient.

A more efficient process is required to purify the paraxylene to meet requirements for use in subsequent chemical processes (e.g. production of terephthalic acid).

The present inventors have surprisingly discovered a process whereby, using crystallization technology, paraxylene may be purified by separating paraxylene both from concentrations of other C8 aromatics and also small concentrations of oxygenated species.

Crystallization technology per se is well-known, and there are numerous permutations of this technology. See, for instance, U.S. Pat. No. 7,439,412. There are also numerous licensed commercial crystallizer technologies, such as the Amoco Process, Maruzen Process, Esso Process, Sulzer Chemtech Process, and the like.

Fractional crystallization in a crystallizer takes advantage of the differences between the freezing points and solubilities of the $C_8$ aromatic components at different temperatures. Due to its higher freezing point, PX is usually separated as a solid in such a process while the other components are recovered in a PX-depleted filtrate. High PX purity, a key property needed for satisfactory commercial conversion of PX to terephthalic anhydrode (PTA) and/or dimethyl terephthalate (DMT) in most plants, can be obtained by this type of fractional crystallization. U.S. Pat. No. 4,120,911 provides a description of this method. A crystallizer that may operate in this manner is described in U.S. Pat. No. 3,662,013.

The present inventors have surprisingly discovered a process using crystallization technology to purify paraxylene having a small but significant quantity of oxygenated species.

SUMMARY OF THE INVENTION

The invention is directed to a process using crystallization technology to purify paraxylene from a mixture of large concentrations of C8 aromatics and also small concentrations of oxygenated species. The present invention is also directed to a process of making said mixture of a large concentration of C8 aromatics and also small concentrations of oxygenated species and then processing said mixture to produce a purified paraxylene.

In embodiments, no clay treatment is needed prior to the purification of the xylene stream by crystallization, and in embodiments such purification can provide paraxylene having a BI less than 30, preferably less than 25, more preferably less than 21.

In embodiments, one or more of the following steps may occur between the alkylation step and the crystallization step: (a) dewatering; (b) solids removal; (c) xylene splitter; and (d) caustic scrubber.

These and other objects, features, and advantages will become apparent as reference is made to the following detailed description, preferred embodiments, examples, and appended claims.

DETAILED DESCRIPTION

A paraxylene-rich stream produced by alkylation of toluene with methanol produces high concentrations of other C8 aromatics (o-xylene, m-xylene, styrene, ethylbenzene, etc.) and low concentrations of oxygenated species (acetic acid, phenol, cresols, etc). The process of the invention provides a higher purity paraxylene stream, having lower amounts of non-paraxylene C8 impurities and lower amounts of oxygenates, which in embodiments, provides an improved feed to subsequent chemical processes, e.g. production of terephthalic acid (TPA).

The present inventors have identified crystallization as a process that simultaneously removes oxygenates and other C8 aromatics. This single-step process is more cost efficient than a separate two-step process.

Crystallization technology has been used to purify paraxylene commercially. The paraxylene streams currently purified using crystallization are not made via alkylation of toluene with methanol and thus do not contain significant concentrations of oxygenates. Any known crystallization technology, particularly any commercially-available technology, may be used downstream of the alkylation step with methanol.

The alkylation process of the invention also is known per se, and is a process comprising contacting a feed comprising methanol with porous crystalline materials, particularly certain porous crystalline materials having specific and closely defined diffusion characteristics, such as can be obtained by unusually severe steaming of ZSM-5 containing an oxide modifier, such materials having improved selectivity for the alkylation of toluene with methanol, and in particularly preferred embodiments a selectivity such that the xylene product contains at least about 90% of the para-isomer at per-pass toluene conversions of at least about 15%.

In one aspect, the invention resides in a process for the selective production of para-xylene which comprises reacting toluene with methanol under alkylation conditions in the presence of a catalyst comprising a porous crystalline material having a Diffusion Parameter for 2,2-dimethylbutane of about 0.1-15 sec-$^{-1}$ when measured at a temperature of 120° C. and a 2,2-dimethylbutane pressure of 60 torr (8 kPa). Preferably, the porous crystalline material has a Diffusion Parameter of about 0.5-10 sec$^{-1}$.

Preferably, the catalyst contains at least one oxide modifier and more preferably at least one oxide modifier selected from oxides of elements of Groups IIA, IIIA, IIIB, IVA, VA, VB and VIA of the Periodic Table. Most preferably the oxide modifier is selected from oxides of boron, magnesium, calcium, lanthanum and most preferably phosphorus.

Preferably, the catalyst contains about 0.05 to about 20, more preferably about 0.1 to about 10 and most preferably about 0.1 to about 5.0 wt % of the oxide modifier based on elemental modifier (e.g., phosphorus when the oxide modifier is $P_2O_5$).

Preferably, the catalyst has an alpha value less than 50 and preferably less than 10. The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

In a further aspect, the invention resides in a method for producing a catalyst for use in the selective production of para-xylene by reacting toluene with methanol, said method comprising the steps of: (a) starting with a porous crystalline material having a Diffusion Parameter for 2,2-dimethylbutane in excess of 15 sec$^{-1}$ when measured at a temperature of 120° C. and a 2,2-dimethylbutane pressure of 60 torr (8 kPa); and (b) contacting the material of step (a) with steam at a temperature of at least about 950° C. to reduce the Diffusion Parameter thereof for 2,2-dimethylbutane to about 0.1-15 sec$^{-1}$ when measured at a temperature of 120° C. and a 2,2-dimethylbutane pressure of 60 torr (8 kPa), the micropore volume of the steamed material being at least 50% of the unsteamed material.

Preferably, said porous crystalline material used in step (a) comprises an aluminosilicate zeolite having a silica to alumina molar ratio of at least 250. The present invention provides a process for alkylating toluene with methanol to selectively produce p-xylene in high yield and with a high per-pass conversion of toluene. The process employs a catalyst which comprises a porous crystalline material having a Diffusion Parameter for 2,2-dimethylbutane of about 0.1-15 sec$^{-1}$, and preferably 0.5-10 sec$^{-1}$, when measured at a temperature of 120° C. and a 2,2-dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value Q/Q∞, where Q∞ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material employed in the process of the invention is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the process of the invention.

Particular examples of suitable medium pore zeolites include ZSM-5, ZSM-11, ZSM-12, ZSM-22, ZSM-23, ZSM-35, ZSM48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM-48 and the conventional preparation thereof is taught by U.S. Pat. No. 4,375,573, the disclosure of which is incorporated herein by reference. MCM-22 is disclosed in U.S. Pat. No. 5,304,698 to Husain; U.S. Pat. No. 5,250,277 to Kresge et al.; U.S. Pat. No. 5,095,167 to Christensen; and U.S. Pat. No. 5,043,503 to Del Rossi et al., the disclosure of which patents are incorporated by reference.

Preferably, the zeolite employed in the process of the invention is ZSM-5 having a silica to alumina molar ratio of at least 250, as measured prior to any treatment of the zeolite to adjust its diffusivity.

The medium pore zeolites described above are preferred for the process of the invention since the size and shape of their pores favor the production of p-xylene over the other xylene isomers. However, conventional forms of these zeolites have Diffusion Parameter values in excess of the 0.1-15 sec$^{-1}$ range required for the process of the invention. The required diffusivity for the present catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the porous crystalline material is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Most preferably, said at least one oxide modifier is selected from oxides of boron, magnesium, calcium, lanthanum and most preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier in the catalyst of the invention is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours.

Similar techniques known in the art can be used to incorporate other modifying oxides into the catalyst of the invention.

Representative phosphorus-containing compounds which may be used to incorporate a phosphorus oxide modifier into the catalyst of the invention include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_n$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2PDX$, such as diethylphosphinous acid, primary, $(RO)P(OX)_2$, secondary, $(RO)_2PDX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)_2PCl$, dialkylphosphinochloroidites, $R_2PCl$, alkyl alkylphosphonochloridates. $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$. $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite. phosphorus trichloride, phosphoric acid, phenyl phosphine oxychloride, trimethylphosphate, diphenyl phosphinous acid, diphenyl phosphinic acid, diethyichlorothiophosphate, methyl acid phosphate, and other alcohol-$P_2O_5$ reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylae, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of the invention may be combined with a variety of binder or matrix materials resistant to the temperatures and other conditions employed in the process. Such materials include active and inactive materials such as clays, silica and/or metal oxides such as alumina The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmoillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be mixed with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20-200 microns.

The catalyst of the invention may optionally be precoked. The precoking step is preferably carried out by initially utilizing the uncoked catalyst in the toluene methylation reaction, during which coke is deposited on the catalyst surface and thereafter controlled within a desired range, typically from about 1 to about 20 wt % and preferably from about 1 to about 5 wt %, by periodic regeneration by exposure to an oxygen-containing atmosphere at an elevated temperature.

One of the advantages of the catalyst described herein is its ease of regenerability. Thus, after the catalyst accumulates coke as it catalyzes the toluene methylation reaction, it can easily be regenerated by burning off a controlled amount of coke in a partial combustion atmosphere in a regenerator at temperatures in the range of from about 400 to about 700° C. The coke loading on the catalyst may thereby be reduced or substantially eliminated in the regenerator. If it is desired to maintain a given degree of coke loading, the regeneration step may be controlled such that the regenerated catalyst returning to the toluene methylation reaction zone is coke-loaded at the desired level.

The present process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

The process of the present invention is generally conducted at a temperature between about 500 and about 700° C., preferably between about 500 and about 600° C., a pressure of between about 1 atmosphere and 1000 psig (100 and 7000 kPa), a weight hourly space velocity of between about 0.5 and 1000, and a molar ratio of toluene to methanol (in the reactor charge) of at least about 0.2, e.g., from about 0.2 to about 20. The process is preferably conducted in the presence of added hydrogen and/or added water such that the molar ratio of hydrogen and/or water to toluene+methanol in the feed is between about 0.01 and about 10.

Using the process of the invention, toluene can be alkylated with methanol so as to produce para-xylene at a selectivity of at least about 90 wt % (based on total $C_8$ aromatic product) at a per-pass toluene conversion of at least about 15 wt % and a trimethylbenzene production level less than 1 wt %.

One of the advantages of the process of the invention is that, in embodiments, the xylenes produced do not require clay treatment prior to crystallizer treatment, which is a great economic advantage. Typical product specifications for paraxylenes produced by other processes require a BI under 200. In the process of the present invention, including the preferred embodiment of no clay treating prior to crystallization, a paraxylene product of crystallization can meet a product specification of BI=20.

Many different crystallizer schemes have been implemented. Almost all schemes use the same concepts in recovering p-xylene as follows: (a) p-xylene feed is cooled, crystallized and separated at a very cold temperature for maximum recovery; then (b) the crystals are melted and recrystallized and separated at a warmer temperature for maximum p-xylene purity.

Preferred crystallizer processes include the following.

Direct Contact Cooling: feed is cooled in a crystallizer vessel by injecting refrigerant, such as $C_2^=$ or $CO_2$ directly into the slurry.

Indirect Contact Cooling: feed is cooled in a jacketed crystallizer vessel. The refrigerant, such as $C_2^=$ or $C_3$, is fed into the jacket. Alternatively, feed can be cooled in a scraped chiller where crystals form inside the chiller. The crystals formed collect in a holdup drum. Indirect contact cooling is slightly less energy efficient than direct cooling, but no refrigerant/feed separation equipment is needed.

Centrifuge or Filtration for Sold/Liquid Separation: either centrifuge or filters are used. Centrifuges are more expensive than filters, however, produce a dryer crystal cake than can be achieve in a filter.

Centrifuge Wash: the warmer crystallization maximizes p-xylene purity. Several of the process schemes use a wash step with the centrifuges of the warmest crystallization stage to replace trapped mother liquor in the crystal cake. This wash can be p-xylene or another component, such as toluene, pentane, or other light hydrocarbon. P-xylene wash has the advantage that no downstream separation system for removing the wash component is required.

Melt Stage: between crystallizer stages, p-xylene crystals are melted into a new xylene stream which is much higher in p-xylene content than the feed was.

One or more of these schemes may be used as part of the crystallizer step(s) of the present invention.

After alkylation and before crystallization, there may also be one or more steps selected from the following: (a) dewatering; (b) solids removal; (c) xylene splitter; and (d) caustic scrubber.

After crystallization, the purified paraxylene fraction is separated and the remaining filtrate may be sent to a caustic scrubber to be upgraded.

The invention will now be more particularly described in the following Examples, which are intended to be representative of the present invention and not limiting thereof Example 1

A xylene stream produced by alkylation of toluene with methanol was purified via two-stage batch crystallization. Analysis of the feed and product streams from this process showed that, not only was the paraxylene content of the stream increased, but the oxygenate content of the stream as measured by the UOP 624 method was also significantly reduced. The UOP 624 method is available, for instance, by subscription from IHS® and is a method of carbonyl number by chemical analysis. What is important is not the exact value obtained but the relative value. Carbonyl analysis may be obtained from many methods publicly available, as would be know by one of skill in the art.

|  | Crystallizer Feed | 2nd Stage Melt |
|---|---|---|
| Xylenes, wt % | 95.0 | 99.4 |
| PX selectivity, % | 89.1 | 98.7 |
| Bromine Index | 218 | 20 |
| Styrene, ppm | 708 | 78 |
| UOP 624, C=O mg/L | 6.2 | 1.1 |
| Acetic acid, ppm | 0.44 | 0.1 |

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention has been described above with reference to numerous embodiments and specific examples. Many variations will suggest themselves to those skilled in this art in light of the above detailed description. All such variations are within the scope of the appended claims.

What is claimed is:

1. A process comprising selective production of paraxylene by the alkylation of benzene and/or toluene with methanol to produce a product stream having high concentrations of C8 aromatics and low concentrations of oxygenate by-products, wherein said process includes a step of removing the oxygenate by-products removal from the product stream and then a step of recovery of the C8 aromatics by simulated counter-current adsorption, wherein said alkylation comprises the contact of benzene and/or toluene with methanol in the presence of a catalyst comprising a porous crystalline material having a Diffusion Parameter for 2,2 dimethylbutane of about 0.1-15 sec$^{-1}$ when measured at a temperature of 120° C. and a 2,2 dimethylbutane pressure of 60 torr (8 kPa), wherein said porous crystalline material has undergone prior treatment with steam at a temperature of at least 950° C. for between about 10 minutes and about 100 hours to adjust the Diffusion Parameter of said material to about 0.1-15 sec$^{-1}$.

2. The process of claim 1, wherein said Diffusion Parameter of said porous crystalline material is about 0.5-10 sec$^{-1}$.

3. The process of claim 1, wherein said porous crystalline material has undergone prior treatment with steam at a temperature of at least 1000° C.

4. The process of claim 3, wherein said treatment with steam reduces the pore volume of the catalyst to not less than 50% of that of the pore volume of the catalyst before said treatment with steam.

5. The process of claim 1, wherein the catalyst contains at least one oxide modifier selected from the group consisting of oxides of elements of Groups IIA, IIIA, IIIB, IVA, IVB, VA and VIA of the Periodic Table.

6. The process of claim 1, wherein the catalyst contains at least one oxide modifier selected from the group consisting of oxides of boron, magnesium, calcium, lanthanum and phosphorus.

7. The process of claim 1, wherein the catalyst contains about 0.1 to about 10 wt. % of the oxide modifier based on the elemental modifier.

8. The process of claim 1, wherein the catalyst has an average particle size of about 20 to 200 microns.

9. A process comprising: (i) selective production of paraxylene by the alkylation of benzene and/or toluene with methanol to produce a product stream having high concentrations of C8 aromatics and low concentrations of oxygenate by-products; then (ii) a step of removing the oxygenate by-products removal from the product stream; then (iii) a step of recovery of the C8 aromatics by simulated counter-current adsorption,
    wherein said alkylation comprises the contact of benzene and/or toluene with methanol in the presence of a catalyst comprising a porous crystalline material having a Diffusion Parameter for 2,2 dimethylbutane of about 0.1-15 sec$^{-1}$ when measured at a temperature of 120° C. and a 2,2dimethylbutane pressure of 60 torr (8 kPa), wherein said porous crystalline material has undergone prior treatment with steam at a temperature of at least 950° C. for between about 10 minutes and about 100 hours to adjust the Diffusion Parameter of said material to about 0.1-15 sec$^{-1}$.

10. The process of claim 9, wherein there is no clay treating step between steps (i) and (iii).

* * * * *

UNITED STATES PATENT AND TRADEMARK OFFICE
CERTIFICATE OF CORRECTION

Page 1 of 1

PATENT NO.         : 8,981,171 B2
APPLICATION NO.    : 13/864946
DATED              : March 17, 2015
INVENTOR(S)        : Mark P. Hagemeister, David L. Johnson and John J. Monson It is certified that error appears in the above-identified patent and that said Letters Patent is hereby corrected as shown below:

In the Claims

In Column 10, Line 40, delete "claim 1" and replace with --claim 6--.

Signed and Sealed this
Fourth Day of August, 2015

Michelle K. Lee
*Director of the United States Patent and Trademark Office*